US009554932B2

(12) United States Patent
Pattison et al.

(10) Patent No.: US 9,554,932 B2
(45) Date of Patent: Jan. 31, 2017

(54) SYSTEM AND METHOD FOR GASTRIC RESTRICTION AND MALABSORPTION

(71) Applicant: EZ-Off Weight Loss, LLC, Leawood, KS (US)

(72) Inventors: Mary Pattison, Kansas City, MO (US); Charles Phillip Pattison, Kansas City, MO (US); Stephen J. Lowry, Kansas City, MO (US); Mark A. Molos, Kansas City, MO (US)

(73) Assignee: EZ-Off Weight Loss, LLC, Leawood, KS (US)

( * ) Notice: Subject to any disclaimer, the term of this patent is extended or adjusted under 35 U.S.C. 154(b) by 282 days.

(21) Appl. No.: 14/216,666

(22) Filed: Mar. 17, 2014

(65) Prior Publication Data
US 2014/0276338 A1    Sep. 18, 2014

Related U.S. Application Data

(60) Provisional application No. 61/790,709, filed on Mar. 15, 2013, provisional application No. 61/862,463, filed on Aug. 5, 2013.

(51) Int. Cl.
*A61F 5/00* (2006.01)

(52) U.S. Cl.
CPC ........... *A61F 5/0079* (2013.01); *A61F 5/0076* (2013.01)

(58) Field of Classification Search
CPC ............................. A61F 5/0076; A61F 5/0079
See application file for complete search history.

(56) References Cited

U.S. PATENT DOCUMENTS

| 4,315,513 A | 2/1982 | Nawash et al. |
| 4,356,824 A | 11/1982 | Vasquez |

(Continued)

FOREIGN PATENT DOCUMENTS

| WO | WO2011/004335 | 1/2011 |
| WO | WO2014/145799 | 9/2014 |
| WO | WO2015/020977 | 2/2015 |

OTHER PUBLICATIONS

International Search Report and Written Opinion Corresponding to International Application No. PCT/US2014/030625, Completed Aug. 1, 2014.

(Continued)

*Primary Examiner* — Leslie Deak
*Assistant Examiner* — Kai Weng
(74) *Attorney, Agent, or Firm* — Lathrop & Gage LLP

(57) ABSTRACT

The present disclosure relates generally to prosthetic devices for use in restricting food and caloric intake into the stomach and of absorption of the food components in the stomach and small intestine. The system includes an elongated bariatric sleeve having a normally superior or upper proximal end and a normally inferior or lower distal end. An elongated lumen support member is positioned within the first lumen in contacting relation with the first membrane for maintaining the first lumen in an open position. A proximal anchor ring with a central aperture and a catheter channel is connected to the proximal end of the sleeve to the collar member. The anchor is inflatable or expandable memory material for anchoring the sleeve in superior relation to a pyloric valve of the patient's stomach. An anchor weight is connected to the distal end of the first flexible tube. The device further includes a tether or a delivery catheter connected to a gastric port to aide in minimizing movement of the device and the device for delivery of nutritional and pharmaceutical compositions through the gastric opening and into the second (Continued)

lumen where they may be absorbed by the proximal duodenum and jejunum of the small intestine. The system can also include an intragastric displacement balloon.

18 Claims, 11 Drawing Sheets

(56) References Cited

U.S. PATENT DOCUMENTS

| | | | |
|---|---|---|---|
| 4,668,225 A | 5/1987 | Russo et al. |
| 5,007,900 A | 4/1991 | Picha et al. |
| 5,071,405 A | 12/1991 | Piontek et al. |
| 5,112,310 A | 5/1992 | Grobe |
| 5,147,316 A | 9/1992 | Castillenti |
| 5,167,627 A | 12/1992 | Clegg et al. |
| 5,259,399 A | 11/1993 | Brown |
| 5,527,280 A | 6/1996 | Goelz |
| 5,716,347 A | 2/1998 | Gibbs et al. |
| 5,720,734 A | 2/1998 | Copenhaver et al. |
| 5,865,816 A | 2/1999 | Quinn |
| 5,993,473 A | 11/1999 | Chan et al. |
| 6,030,361 A | 2/2000 | Miyashiro |
| 6,419,670 B1 | 7/2002 | Dikeman |
| 6,454,785 B2 | 9/2002 | De Hoyos Garza |
| 6,551,270 B1 | 4/2003 | Bimbo et al. |
| 6,907,992 B2 | 6/2005 | McMichael et al. |
| 6,910,581 B2 | 6/2005 | McMichael et al. |
| 7,025,791 B2 | 4/2006 | Levine et al. |
| 7,122,058 B2 | 10/2006 | Levine et al. |
| 7,220,284 B2 | 5/2007 | Kagan et al. |
| 7,267,694 B2 | 9/2007 | Levine et al. |
| 7,314,489 B2 | 1/2008 | McKenna et al. |
| 7,316,716 B2 | 1/2008 | Egan |
| 7,329,285 B2 | 2/2008 | Levine et al. |
| 7,347,875 B2 | 3/2008 | Levine et al. |
| 7,476,256 B2 | 1/2009 | Meade et al. |
| 7,563,254 B2 | 7/2009 | Delegge |
| 7,678,068 B2 | 3/2010 | Levine et al. |
| 7,682,330 B2 | 3/2010 | Meade et al. |
| 7,695,446 B2 | 4/2010 | Levine et al. |
| 7,758,535 B2 | 7/2010 | Levine et al. |
| 7,766,861 B2 | 8/2010 | Levine et al. |
| 7,766,973 B2 | 8/2010 | Levine et al. |
| 7,794,447 B2 | 9/2010 | Dann et al. |
| 7,806,870 B2 | 10/2010 | Mastri et al. |
| 7,815,591 B2 | 10/2010 | Levine et al. |
| 7,819,836 B2 | 10/2010 | Levine et al. |
| 7,824,368 B2 | 11/2010 | Clem et al. |
| 7,833,156 B2 | 11/2010 | Williams et al. |
| 7,833,202 B2 | 11/2010 | Suzuki |
| 7,837,643 B2 | 11/2010 | Levine et al. |
| 7,935,073 B2 | 5/2011 | Levine et al. |
| 7,976,488 B2 | 7/2011 | Levine et al. |
| 7,981,163 B2 | 7/2011 | Meade et al. |
| 8,057,420 B2 | 11/2011 | Meade et al. |
| 8,096,966 B2 | 1/2012 | Levine et al. |
| 8,097,000 B2 | 1/2012 | Albrecht |
| 8,109,910 B2 | 2/2012 | Zastawny et al. |
| 8,109,943 B2 | 2/2012 | Boraiah et al. |
| 8,137,301 B2 | 3/2012 | Levine et al. |
| 8,147,454 B2 | 4/2012 | Watanabe et al. |
| 8,147,561 B2 | 4/2012 | Binmoeller |
| 8,162,871 B2 | 4/2012 | Levine et al. |
| 8,182,459 B2 | 5/2012 | Dann et al. |
| 8,206,456 B2 | 6/2012 | Stack et al. |
| 8,211,186 B2 | 7/2012 | Belhe et al. |
| 8,246,617 B2 | 8/2012 | Welt et al. |
| 8,303,669 B2 | 11/2012 | Meade et al. |
| 8,430,811 B2 | 4/2013 | Hess et al. |
| 2002/0042607 A1 | 4/2002 | Palmer et al. |
| 2002/0055757 A1 | 5/2002 | Torre et al. |
| 2003/0097099 A1 | 5/2003 | Quinn |
| 2003/0158569 A1 | 8/2003 | Wazne |
| 2003/0225393 A1 | 12/2003 | McMichael et al. |
| 2004/0059289 A1 | 3/2004 | Garza Alvarez |
| 2005/0240279 A1 | 10/2005 | Kagan et al. |
| 2005/0267415 A1 | 12/2005 | Jacques |
| 2006/0030872 A1 | 2/2006 | Culbert et al. |
| 2007/0123840 A1 | 5/2007 | Cox |
| 2007/0156165 A1 | 7/2007 | Chang et al. |
| 2007/0225728 A1 | 9/2007 | Stefanchik et al. |
| 2007/0255257 A1 | 11/2007 | Willis et al. |
| 2008/0249474 A1 | 10/2008 | Baker |
| 2009/0204067 A1 | 8/2009 | Abu-Halawa |
| 2009/0299486 A1 | 12/2009 | Shohat et al. |
| 2010/0081875 A1 | 4/2010 | Fowler et al. |
| 2010/0081883 A1 | 4/2010 | Murray et al. |
| 2010/0152764 A1 | 6/2010 | Merkle |
| 2010/0249822 A1 | 9/2010 | Nihalani |
| 2010/0280368 A1 | 11/2010 | Can et al. |
| 2010/0312047 A1 | 12/2010 | Forsell |
| 2010/0324375 A1 | 12/2010 | Piskun |
| 2010/0331756 A1 | 12/2010 | Meade et al. |
| 2011/0046537 A1 | 2/2011 | Errico et al. |
| 2011/0082442 A1 | 4/2011 | Solovay et al. |
| 2011/0106273 A1 | 5/2011 | Belhe et al. |
| 2011/0160539 A1 | 6/2011 | Robertson |
| 2011/0245751 A1 | 10/2011 | Hoffmann |
| 2011/0257580 A1 | 10/2011 | Meade et al. |
| 2011/0276091 A1 | 11/2011 | Melanson et al. |
| 2011/0301523 A1 | 12/2011 | Levine et al. |
| 2012/0029413 A1 | 2/2012 | Meade et al. |
| 2012/0078174 A1 | 3/2012 | Tai et al. |
| 2012/0095495 A1 | 4/2012 | Babkes et al. |
| 2012/0116362 A1 | 5/2012 | Kieturakis |
| 2012/0132212 A1 | 5/2012 | Nishtala |
| 2012/0184967 A1 | 7/2012 | Levine et al. |
| 2012/0203271 A1 | 8/2012 | Larkin et al. |
| 2012/0215152 A1 | 8/2012 | Levine et al. |
| 2012/0232339 A1 | 9/2012 | Csiky |
| 2012/0323081 A1 | 12/2012 | Son |
| 2013/0012862 A1 | 1/2013 | Meade et al. |
| 2013/0041231 A1 | 2/2013 | Bonadio et al. |
| 2013/0041372 A1 | 2/2013 | Welt et al. |
| 2013/0060091 A1 | 3/2013 | Azarbarzin et al. |
| 2013/0066304 A1 | 3/2013 | Belson et al. |
| 2013/0102876 A1 | 4/2013 | Limon et al. |
| 2013/0211196 A1 | 8/2013 | Belson et al. |
| 2015/0038794 A1 | 2/2015 | Pattison et al. |

OTHER PUBLICATIONS

International Search Report and Written Opinion of the International Searching Authority Corresponding to International Application No. PCT/US2014/049639, Completed Nov. 12, 2014.

International Search Report and Written Opinion of the International Searching Authority Corresponding to International Application No. PCT/US14/67689, Completed Mar. 30, 2015.

International Search Report and Written Opinion of the International Searching Authority Corresponding to International Application No. PCT/US14/67697, Completed Mar. 30, 2015.

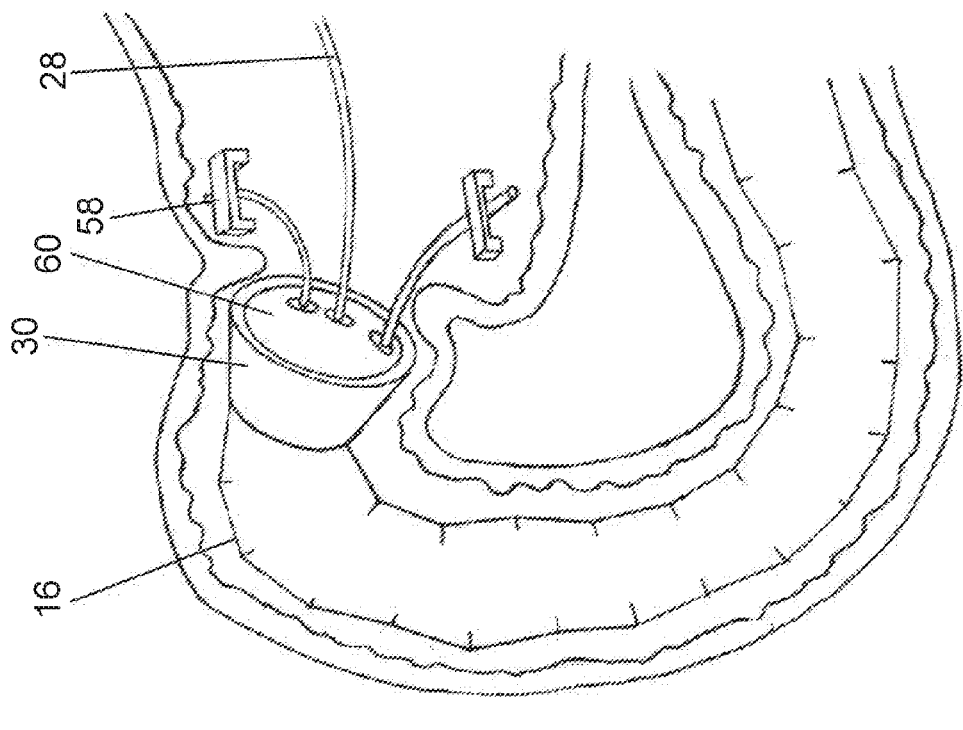
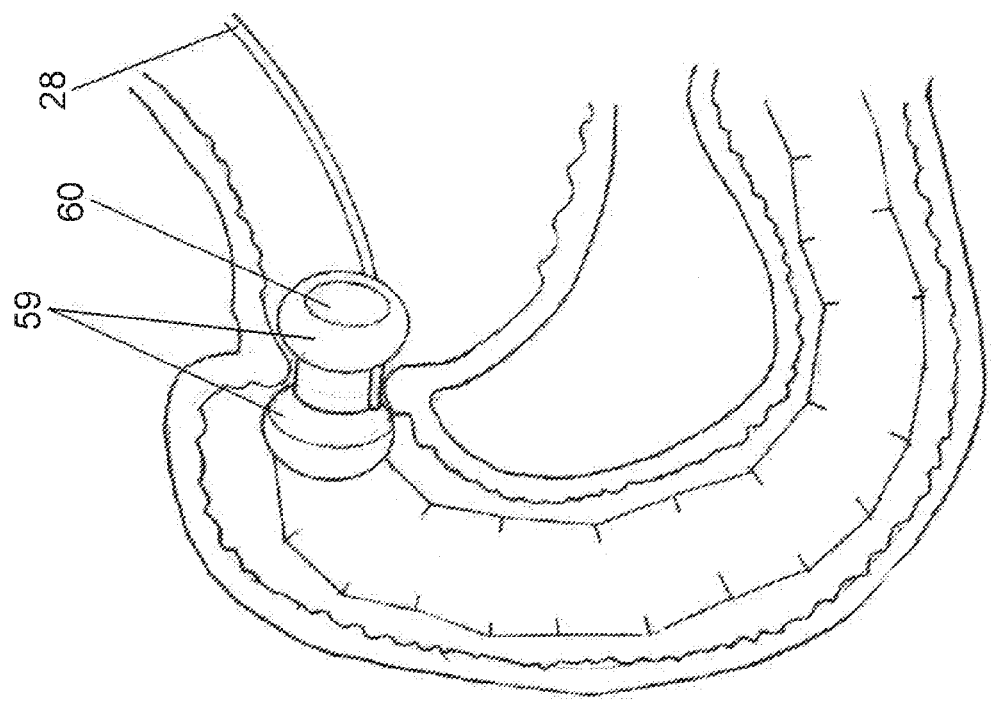
FIG. 11

SYSTEM AND METHOD FOR GASTRIC RESTRICTION AND MALABSORPTION

This application relates to and claims priority to U.S. Provisional Patent Applications No. 61/790,709 and 61/862,463, which were filed Mar. 15, 2013 and Aug. 5, 2013 respectively and are incorporated herein by reference in their entirety.

FIELD

The present disclosure relates generally to prosthetic devices for use in restricting food and caloric intake into the stomach and of absorption of the food components in the stomach and small intestine. More particularly, it concerns a gastrointestinal sleeve that is delivered via an endoscope introduced through percutaneous gastrostomy.

BACKGROUND

In recent years obesity and related disorders, such as diabetes and atherosclerotic cardiovascular disease, have increased substantially. When compliance with diet, exercise and behavioral therapy fail to achieve weight loss, pharmacotherapy may be instituted. However, pharmacotherapy has had only modest success and may be discontinued if a patient experiences unpleasant side-effects. Long term safety of pharmaceutical use for treatment of obesity is uncertain, and patients generally regain lost weight when the therapy is discontinued. A variety of surgical treatments have recently become available for obesity, but typically as a last resort. These surgical treatments have the advantage of more rapid initial weight loss and remission of diabetes mellitus than other non-invasive therapies. However, surgery is expensive, subject to risks of morbidity and mortality, and its efficacy may be reduced by patient noncompliance with post-surgical dietary restrictions. If patients fail to limit food intake, their bodies may undergo compensatory anatomical changes that partially overcome the effects of surgery. The most invasive surgical procedures tend to achieve the greatest long term percent change in weight, but also tend to be the most costly, require longer periods of recuperation and careful long term management of nutrients to avoid malnutrition.

There have been attempts to achieve the benefits of surgery using minimally invasive procedures that employ various medical devices. Current medical device therapy for obesity and metabolic disease includes insertion of tubular prosthetic barrier devices into the stomach and/or small intestine. However, these bariatric sleeve devices are generally inserted surgically or endoscopically, and any modification or removal necessitates additional surgical or endoscopic procedures. Bariatric sleeve devices generally consist of a floppy, elongated tube that is attached at the proximal end to a portion of the stomach or small intestine by suturing or use of a barbed anchor. The sleeve extends distally into at least a portion of the small intestine. Consumed food passes into and through the tube, which prevents absorption by adjacent portions of the small intestine.

These devices are generally anchored at the proximal end by a metal cage structure which is placed in a portion of the stomach or duodenum. Such attachments are near the proximate end of the device and subject to movement allowing seepage of nutrients and overall ineffectiveness of the device. Peristalsis in the small intestine generally makes similar anchoring of the device at the distal end difficult or impossible. In the small intestine, the uncontrolled distal end is subject to displacement by peristaltic contractions, which may contribute to observed distal migration or proximal invagination. These problems serve to limit sleeve length, and the corresponding effectiveness of the device. Bariatric sleeves are constructed of an impermeable material in order to effectively prevent absorption of food through the sleeve. However, this construction also prevents absorption of some nutrients, which necessitates patient supplementation with vitamins and minerals in order to avoid malnutrition. However, such supplementation is difficult because orally administered supplements may be blocked from absorption by the impermeable sleeve. Alternate methods, such as intravenous administration, are invasive and generally cannot be self-administered.

Thus, there is a need for a system and method for the treatment of obesity that may be easily inserted, positioned, modified and removed from a patient using minimally invasive techniques, that includes a shape-retaining structure to facilitate placement and to avoid collapse and displacement, that provides distal control to avoid forward and distal migration and proximal invagination or eversion, as well as preventing rotation or twisting at points along the sleeve and that provides for easy delivery, effective absorption, and control of nutritional supplements.

SUMMARY

The present disclosure provides a greatly improved system for treatment of obesity by providing an endoluminal weight loss device for gastric restriction and malabsorption in a patient having a gastrostomy, or opening into the stomach from an external body surface. The system includes an elongated bariatric sleeve having a normally superior or upper proximal end and a normally inferior or lower distal end. The device will include at least one sleeve having at least a single lumen that is not permeable to food, but having similar characteristics as a dialysis membrane, to permit water, vitamins, minerals, nutritional supplements and pharmaceutical compositions to pass into the duodenum of the small intestine, while effectively blocking the passage of food. The single sleeve may also include an opening or port to allow local administration of such substances into the duodenum, or it may be fenestrated with a series of spaced apart small apertures, pores or small slits to enable such substances to pass into the duodenum while blocking food absorption. The sleeve can be a single lumen or double lumen design that includes inner and outer elongated flexible tubular membranes. The first or inner membrane has a normally superior or upper proximal end, a normally inferior or lower distal end and a food-impermeable sidewall defining a first lumen. The second or outer membrane circumscribes or encircles the first membrane and includes a normally superior or proximal end, a normally inferior or distal end and a permeable sidewall defining a second lumen between the inner and outer membranes. The permeable sidewall includes an aperture for providing external access to the second lumen. Alternatively, the second or outer membrane could be separate and eccentrically placed tubular membrane which includes a normally superior or proximal end, a normally inferior or distal end and a permeable sidewall defining a second lumen adjacent to the first lumen. The permeable sidewall includes an aperture for providing external access to the second lumen. Alternatively, the permeable sidewall may be fenestrated with a series of spaced apart openings or slits that may extend along part or all of the length of the sidewall. An elongated lumen support member is positioned within the first lumen in contacting relation with the first membrane for maintaining the first lumen in an open position. A proximal anchor ring with a central aperture and a catheter channel is connected to the proximal end of the sleeve. The anchor is inflatable or expandable memory material for anchoring the sleeve in superior relation to a pyloric valve of the patient's stomach. An anchor weight is connected to the distal end of the first flexible tube. A delivery catheter passes from the gastric opening, through the catheter channel in the proximal anchor and to the outer membrane connection in the permeable sidewall aperture for delivery of nutritional and pharmaceutical compositions through the gastric opening and into the second lumen where they may be absorbed by the proximal duodenum and jejunum of the small intestine.

The device may also include an intragastric displacement balloon fillable with a gas or liquid saline solution to partially fill the stomach and impart a feeling of fullness to the patient. A tether member may be provided to connect the displacement balloon with the gastric opening to aide in anchoring and the prevention of movement. The tether may also be connected to the proximal anchor of the bariatric sleeve and/or the gastric port. The device may also include a feeding tube and port configured to deliver water, nutrition elements, and other desired elements to the patient. The feeding tube can be incorporated into a sleeve design that is a single lumen or double lumen configuration. In a single lumen configuration the feeding tube can be positioned in an adjacent configuration to the single lumen of the sleeve. In a double lumen configuration the feeding tube will be positioned intermediate the first tube (inner membrane) and second tube (outer membrane) to allow the delivery of nutrients into the lumen space intermediate the first tube and second tube.

A method of treating obesity in a patient involves providing a bariatric malabsorption device, positioning the device so that it extends into the duodenum and jejunum to prevent absorption of consumed food from the device, and delivering a nutritional supplement into a permeable portion of the device for absorption of nutritional supplements by the patient. The device includes an elongated sleeve having a proximal end and a distal end. The sleeve includes coaxial first or inner and second or outer elongated flexible tubes. The first tube has a proximal end, a distal end and a food-impermeable sidewall defining a first lumen. The second tube circumscribes or encircles the first tube or is a separately adjacent tube and includes a proximal end, a distal end and a permeable sidewall defining a second lumen between the first and second tubes. The permeable sidewall includes a window or port for providing external access to the second lumen. An elongated helical memory member is positioned within the first lumen in contacting relation with the first tube for maintaining the first lumen in an open position. A proximal anchor ring with a central aperture is connected to the proximal end of the sleeve. An anchor weight is connected to the distal end of the first flexible tube. A delivery tube is positionable between the gastric opening or via a subcutaneous port and the permeable sidewall aperture for delivery of materials to the space exterior of the first tube, and alternatively the space intermediate the first and second tube.

An endoscope or other suitable device is advanced through the first lumen of the device to grasp the distal anchor weight(s). The portion of the endoscope with the grasped device is advanced through the gastric opening and into the duodenum and jejunum of the patient while the proximal anchor ring is positioned in contact or adjacent to the gastric antrum, prepyloric area, or just distal to the pylorus. The anchor ring allows for the anchoring of the sleeve in relation to the pyloric valve. The endoscope is caused to release the distal anchor weight and is then withdrawn through the first lumen and the gastric opening. A user employs the delivery tube to introduce a nutritional composition through the gastric opening or subcutaneous port and into the second lumen between the impermeable sidewall of the first tube and the permeable sidewall of the second tube.

Various objects, features and advantages of this disclosure will become apparent from the following detailed description, which, taken in conjunction with the accompanying drawings, which depict, by way of illustration and example, certain embodiments of this system and apparatus. The drawings constitute a part of this specification, include exemplary embodiments of the disclosure, and illustrate various objects and features thereof.

BRIEF DESCRIPTION OF THE DRAWINGS

FIG. 11 is a view of embodiments of the proximal end of the malabsorption device.

DETAILED DESCRIPTION

As required, detailed embodiments of the system for gastric restriction and malabsorption are disclosed herein. However, the disclosed embodiments are provided for illustration only and are merely exemplary of the system, which may be embodied in various forms. Therefore, specific structural and functional details disclosed herein are not to be interpreted as limiting, but merely as a basis for the claims and as a representative basis for teaching one skilled in the art to variously employ the system in virtually any appropriately detailed structure.

Figure 1:
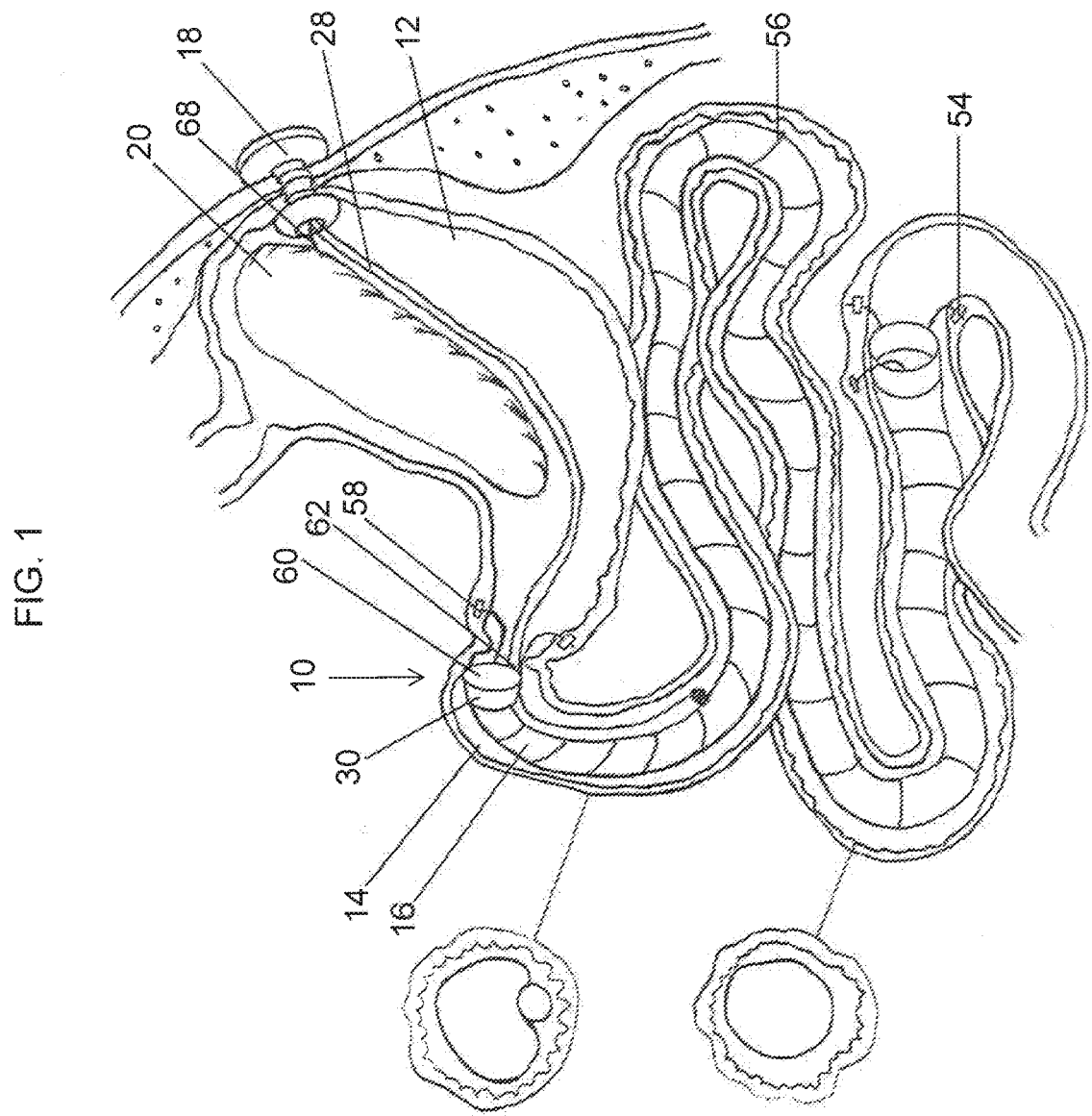
FIG. 1 is a side elevational view of a gastric restriction and malabsorption device in accordance with the disclosure, illustrating the device installed within the stomach and duodenum of a patient.

Referring now to the drawing figures, the reference numeral 10 refers to a system for gastric restriction and malabsorption, which is illustrated in FIG. 1 following deployment in a human stomach 12 and small intestine 14. The system 10 broadly includes a malabsorption sleeve 16, a tether and/or feeding tube connected to an external opening or side port 18 into the stomach 12, a proximal end with at least one anchor mechanism, a distal anchor, and an optional intra-gastric or restriction balloon 20.

Figure 3:
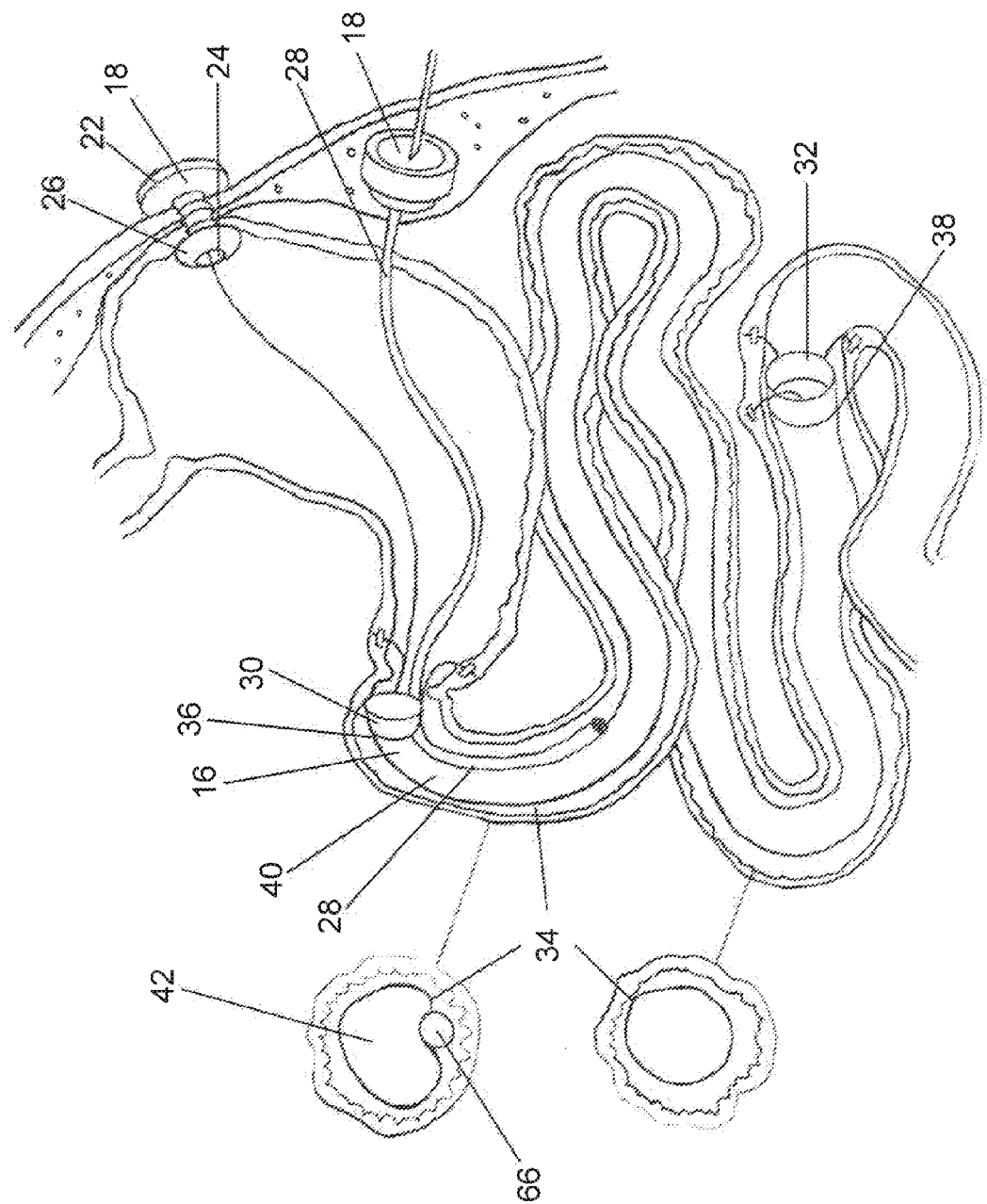
FIG. 3 is an embodiment of the malabsorption device with a cross section view and the addition of the tether and feeding tube.

As best shown in FIGS. 1 and 3, the external port 18 (gastric port) may be formed in any suitable manner, including conventional surgery, interventional radiology, minimally invasive percutaneous endoscopic gastrostomy (PEG), or other percutaneous gastrostomy procedure(s). The port 18 may be of any construction as known in the industry, including but not limited to conventional "button-balloon" construction, inflatable bolster construction, solid bolster construction or combinations thereof. The port 18 includes an exterior positioning element or button 22 having one or more access portals 24, an interior positioning element 26, which may or may not be of inflatable construction and a tube or catheter 28 that extends between the portals 24 and the sleeve 16 as will be described in more detail. In one embodiment, the access port 18 includes adjustability structure (not shown) for enlarging and contracting the diameter of the port, allowing it to receive instruments such as an endoscope, stapler, suturing materials or large gauge tubing. In another embodiment, the access port 18 is positioned beneath the skin of the patient. In such embodiments the exterior and interior positioning elements 22 and 26 may be omitted. In still another embodiment, a second access port 18 may be formed to permit simultaneous access by a plurality of instruments or devices as well as simultaneous access from more than one position. The configuration of the port allows for communication with the catheter that further communicates with the malabsorption sleeve.

Figure 2:
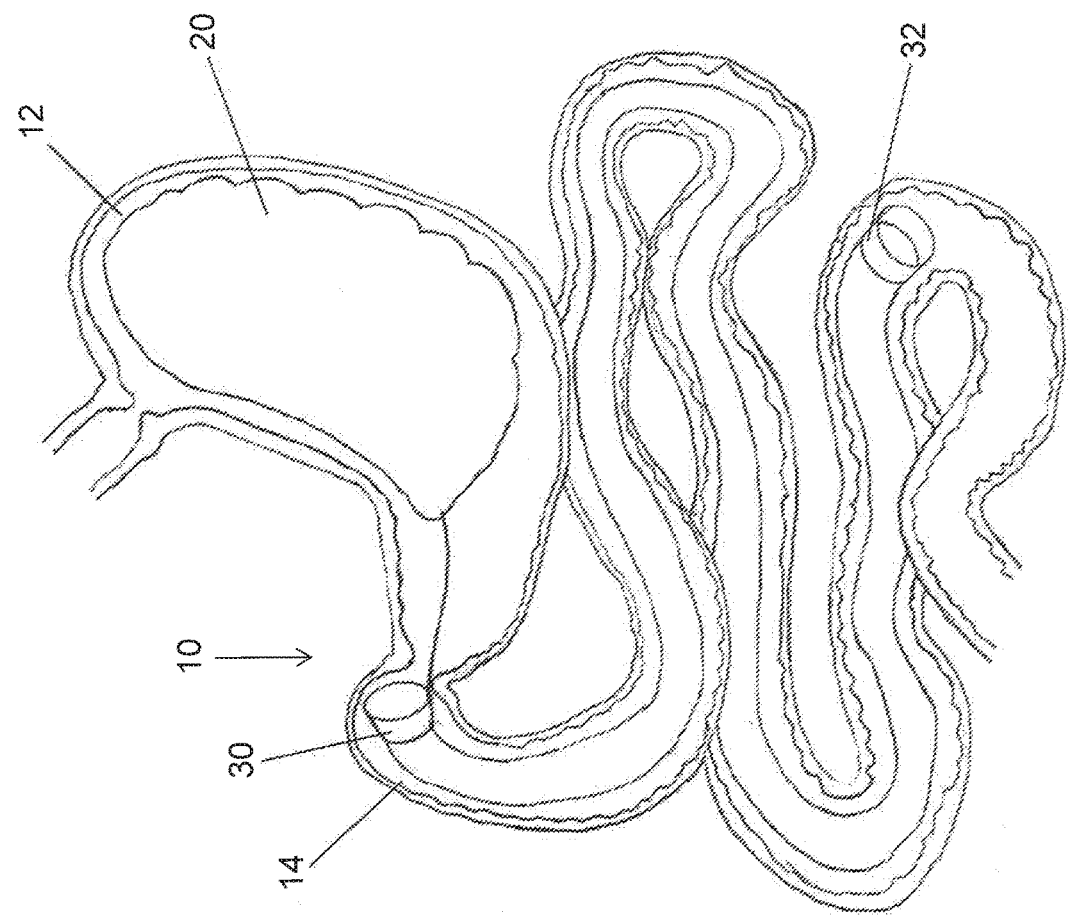
FIG. 2 is a side elevational view of the gastric restriction and malabsorption device.
Figure 4:
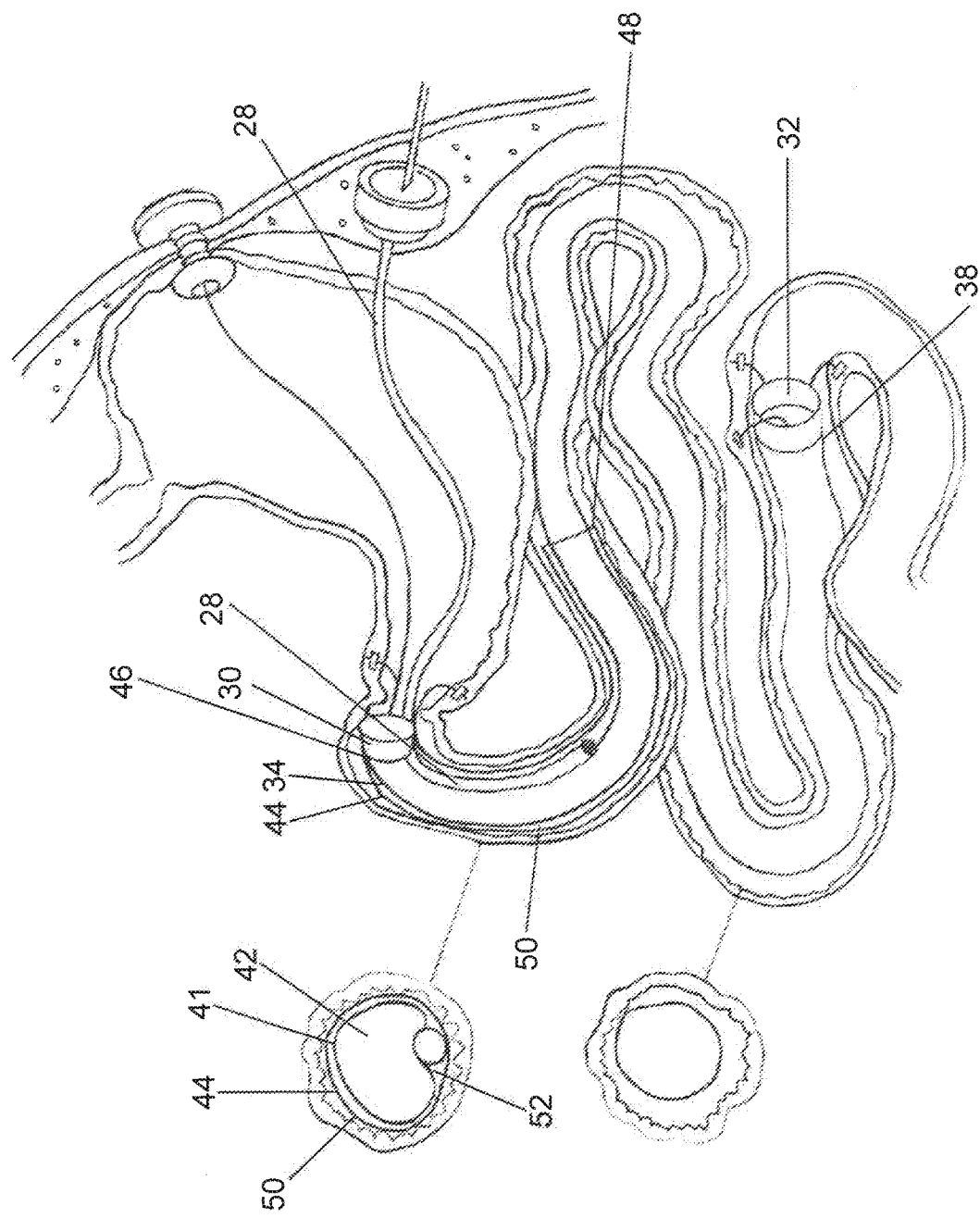
FIG. 4 is an embodiment of the malabsorption device with a double lumen configuration and cross section view.
Figure 5:
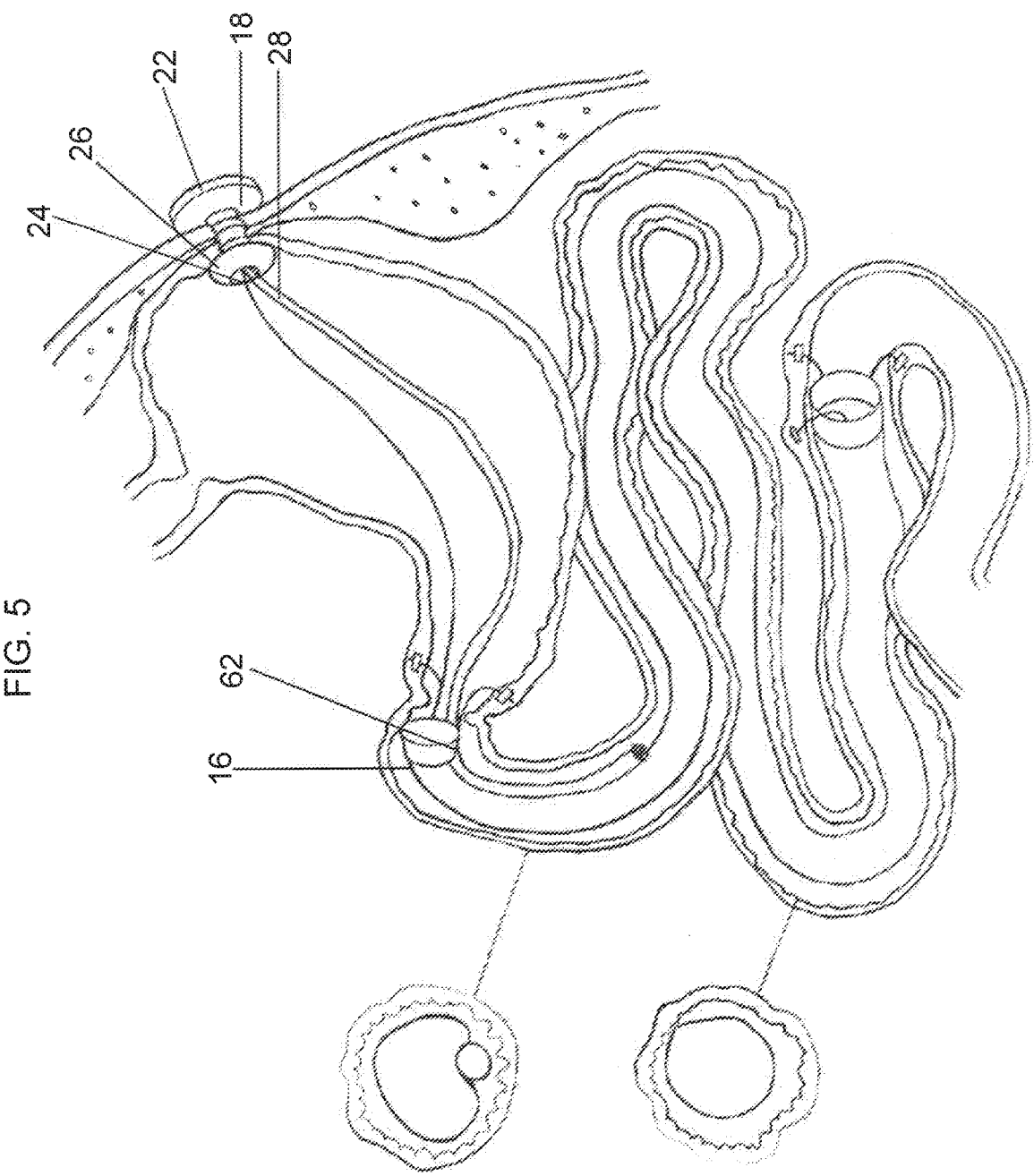
FIG. 5 is an embodiment of the malabsorption device with the tether and feeding tube.

The malabsorption sleeve 16 (FIGS. 1 and 2) includes a proximal or upper end with a collar member 30 and a distal or lower end 32. The sleeve 16 is configured to include a single tube design or a multiple tube design (FIGS. 3 and 4). The collar member 30 can be a removable or integrated configuration with the sleeve 16. In one embodiment the sleeve 16 is a single tube configuration The sleeve includes a flexible tube or membrane 34, configured for connection to the collar member 30, having a proximal end 36, a distal end 38 and a sidewall 40 there between defining a lumen 42. The membrane 34 is of permeable, semipermeable (selectively permeable), or non-permeable construction, to allow passage of nutritional supplements such as vitamins, minerals, and pharmaceutical compositions into the duodenum of the small intestine for absorption. The membrane permeability will depend on the desired absorption rate of products passing through the membrane. In particular the permeability may depend on the solute size, solubility, elemental properties, or chemistry of the elements. In an additional embodiment, the membrane 34 can be divided into sections where a section of the membrane 34 is permeable, a section is semipermeable, and a section is non-permeable. The configuration can be tailored to specific criteria based on the desired absorption rate. The membrane 34 may be of any suitable width and length, with a length of from about 50 cm to about 500 cm, preferably about 75 cm to about 400 cm, more preferably from about 100 cm to about 300 cm.

In another embodiment the sleeve 16 is configured to include a multi-tube design (FIG. 4). The sleeve is configured for connection to the collar 30 and can include a first or interior elongated flexible tube or membrane 34 having a proximal end 36, a distal end 38 and a sidewall 40 there between defining a lumen 42. A second or exterior elongated flexible tube 44 is configured for connection to the collar 30 and encircles a coextensive portion of the first tube 34. In one aspect, the second tube 44 encircles or circumscribes the first tube 34 in coaxial relation. The second or exterior tube or membrane 44 includes a proximal end 46, a distal end 48 and a sidewall 50 there between defining a lumen 52. The interior and outer membrane can be of permeable, semipermeable (selectively permeable), or non-permeable construction, to allow passage of nutritional supplement such as vitamins, minerals, and pharmaceutical compositions into the duodenum of the small intestine, for absorption, dependent on the desired characteristic of the sleeve. In one embodiment, the interior membrane 34 is of impermeable construction, or it may be of semipermeable construction so as to prevent absorption of consumed food but allow passage of water out of the lumen 42 and into the small intestine 14 where it can be absorbed. The outer membrane 44 is of permeable or semipermeable construction, to allow passage of nutritional supplements such as vitamins, minerals such as iron, and pharmaceutical compositions from the lumen 52 into the duodenum of the small intestine 14, for absorption.

The proximal ends of the inner and outer membranes 36 and 46 are connected to form the proximal end with connection to the collar 30 of the sleeve 16. The inner membrane 36 is designed to cause malabsorption of consumed food by serving as a barrier between the food and the upper portion of the small intestine 14, where much chemical digestion takes place. The inner membrane 36 may be of any suitable width and length, with a length of from about 50 cm to about 500 cm, preferably about 75 cm to about 400 cm, more preferably from about 100 cm to about 300 cm. The outer membrane 46 is designed to allow nutritional supplementation of the patient so that malnutrition does not occur. The outer membrane 46 may be of any suitable length, with a length of from about 2 cm to about 100 cm, and preferably from 10 cm to about 50 cm. It is also foreseen that the length of the outer membrane 46 may be coextensive with the inner membrane 36. Except where the lengths of the membranes 36 and 46 are coextensive, the outer membrane 46 terminates before it reaches the distal end 48 of the exterior membrane 44, which continues on to form the distal end 38 of the sleeve 16.

Figure 10:
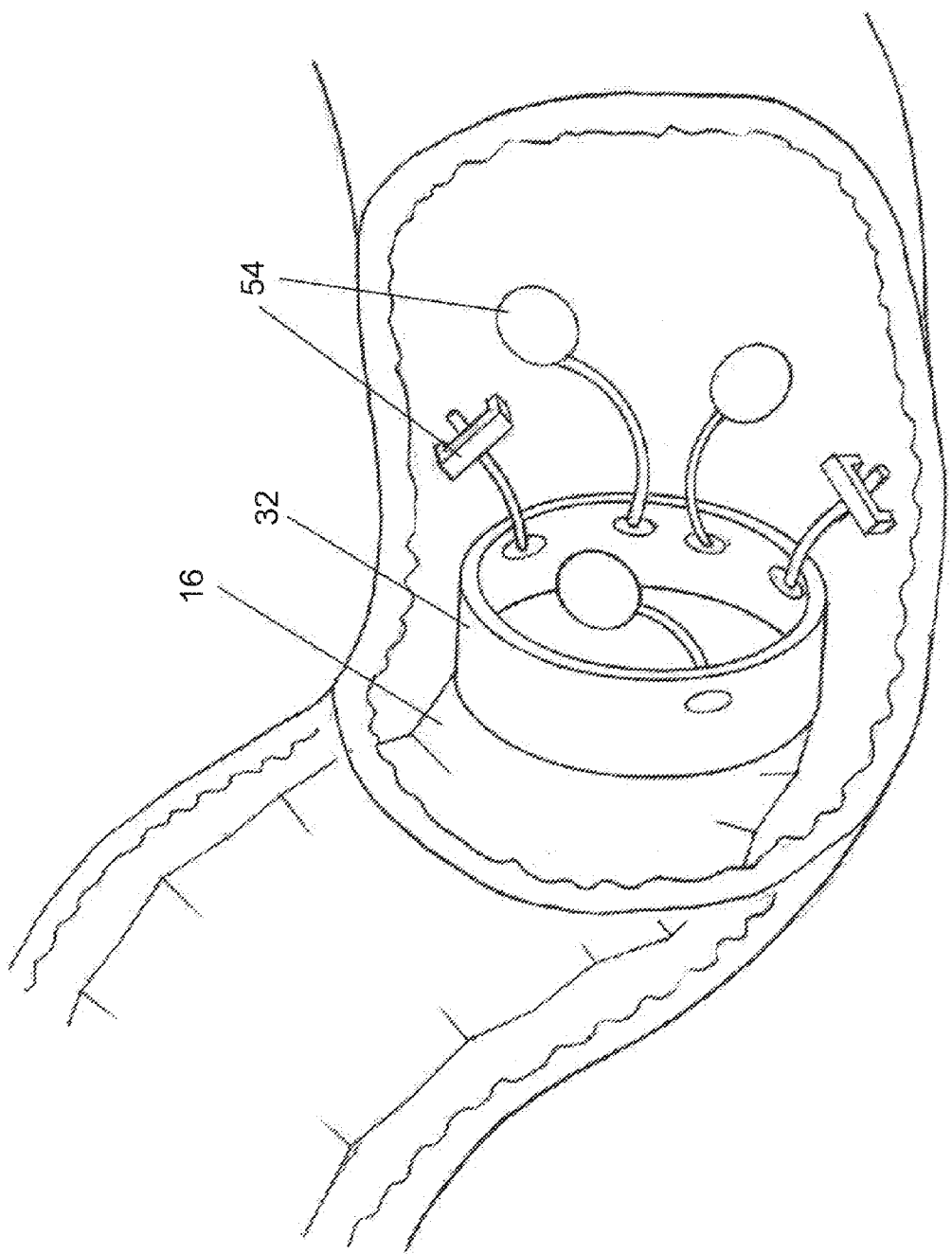
FIG. 10 is a view of the distal end of the malabsorption device.

The distal end 32 of the sleeve 16 includes a distal anchor or weight 54 for preventing proximal migration of the end during peristalsis or physical activity of the patient (FIG. 10). In one embodiment a single weight 54 may be employed, having an annular or any other suitable configuration, or a plurality of weights may be disposed in spaced relation around the perimeter margin of the distal end 32. The weights may be constructed of any suitable material such as a medical grade synthetic resin or metal. In another embodiment an anchor mechanism can be used that allows for the distal end 32 to be attached to the small intestine. The anchor mechanism for attachment can be any method known in the art that includes but is not limited to stapling, suturing, endoclips, T-Tags, tissue glue, or any combinations thereof. In another embodiment the anchor can be a combination of an attachment mechanism and a weight. The attachment mechanism can be a temporary attachment that allows for the attachment of the distal end 32 to the small intestine for a temporary amount of time and after such the weight element will cause the distal end to further migrate down the small intestine until the sleeve is full deployed or unfurled. In a further embodiment when the sleeve 16 includes an outer membrane 46 and inner membrane 36 both the outer and inner membranes include a distal anchor or weight.

Figure 6:
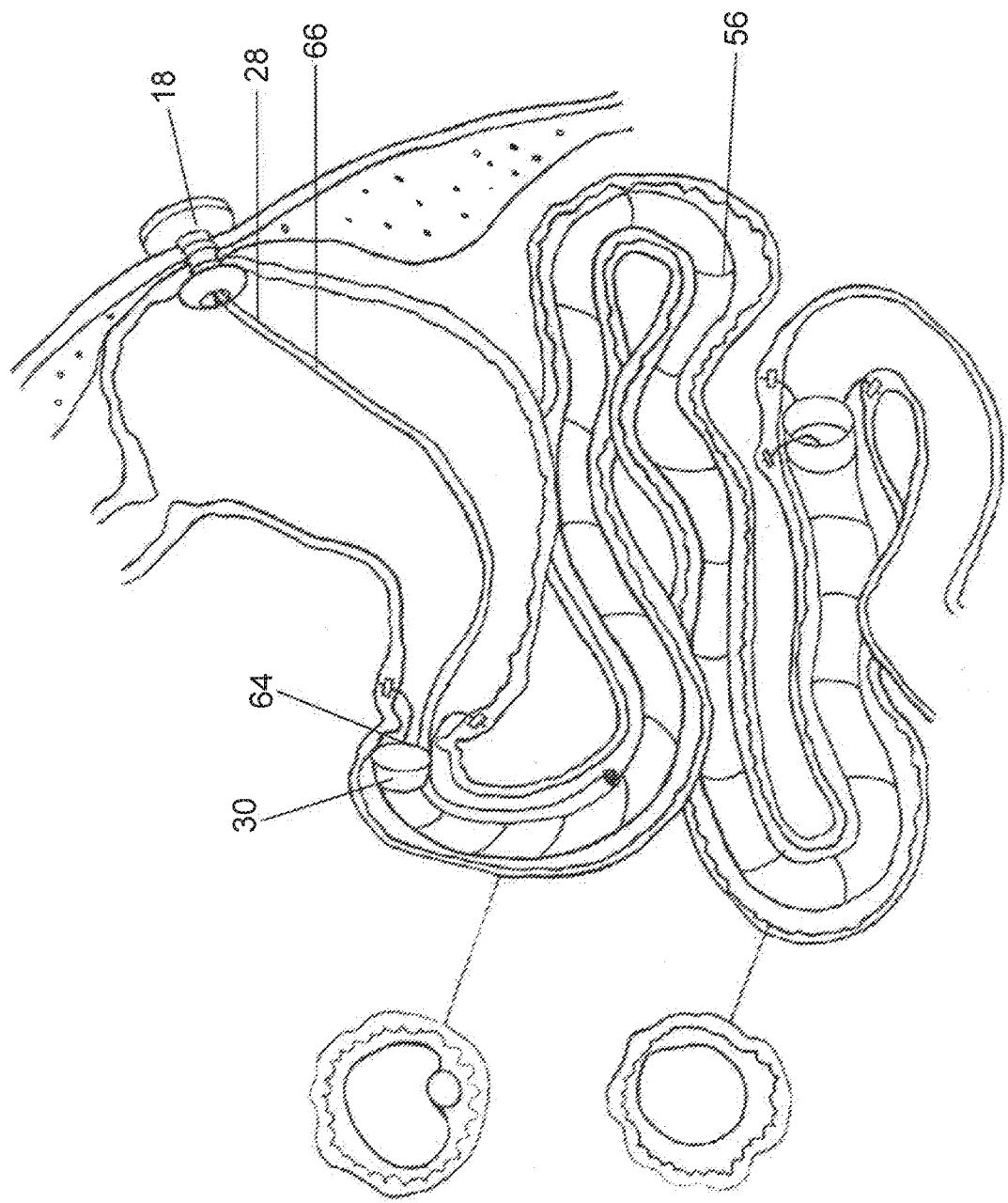
FIG. 6 is an embodiment of the malabsorption device with the feeding tube.
Figure 7:
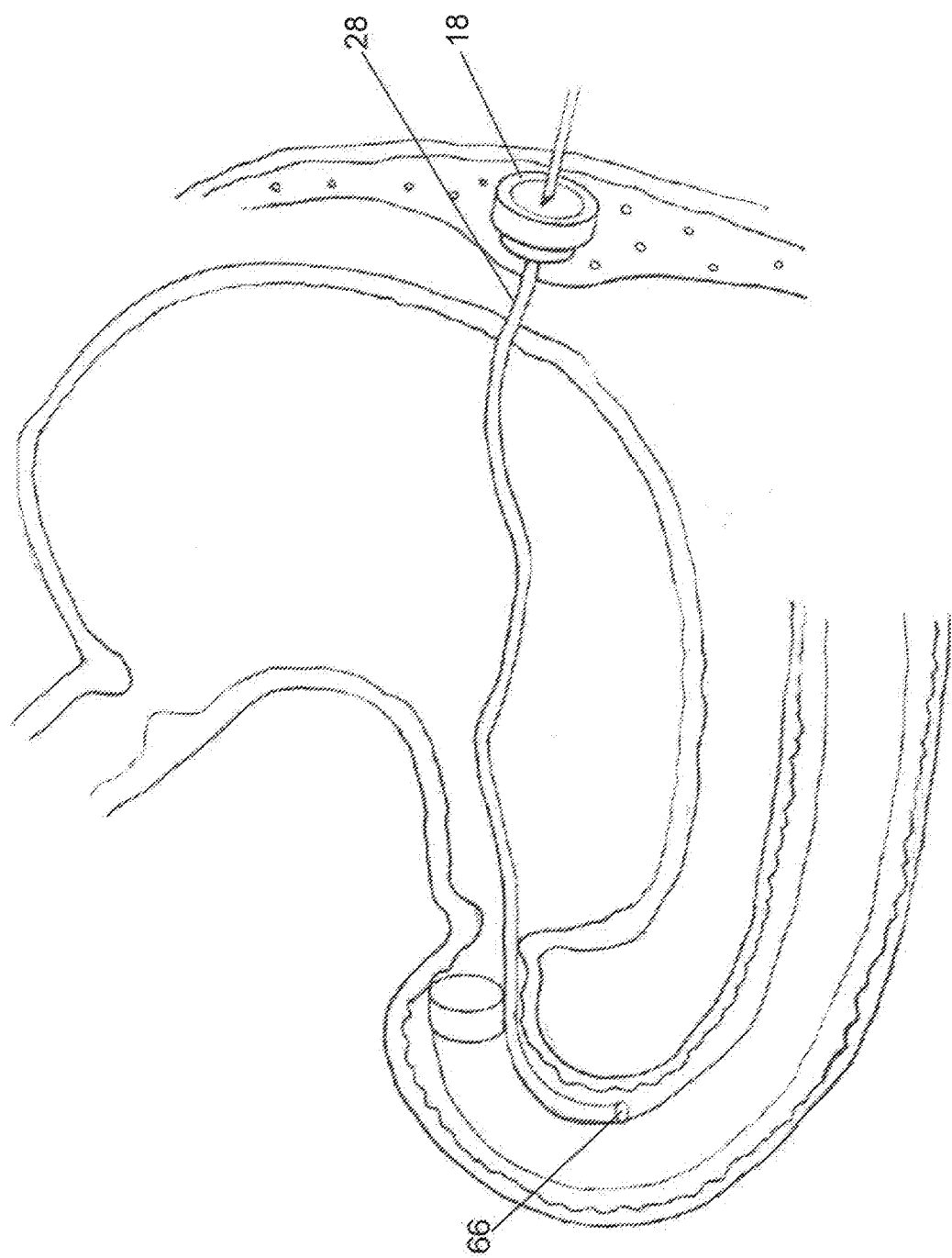
FIG. 7 is an embodiment of the malabsorption device with the feeding tube.

A lumen support element 56 is positioned within the sleeve 16 (FIGS. 1 and 6). In one embodiment it is within the inner lumen 42 to keep the lumen open. In another embodiment the lumen support element 56 is within the single sleeve configuration. The configuration of the lumen support element(s) can be any method known within the industry for support of the interior of the sleeve or other known memory material for such support. In one embodiment, the support element 56 may be configured as a coil, which may be generally spiral, serpentine or helical. In another embodiment, the support element may be configured as a series of spaced apart rings, which may be generally annular, toroid, or quoit shaped. The lumen support 56 preferably extends from the sleeve proximal end and/or collar 30 to the distal end 32, where it may or may not be connected with the collar 30 or the distal anchor weight 54. In certain embodiments the lumen support 56 may extend substantially from the sleeve proximal end to the distal end, terminating a short distance short of the distal end 32. The lumen support 56 may be constructed of any material capable of being formed into a shape-retaining support, such as a synthetic resin or so-called "memory" resin, metal or any other suitable material. In an alternate construction, the inner lumen 42 is constructed of a nonpermeable memory-type material that is capable of resuming its original shape following compression without the need for a lumen support element 56. The membrane may be formed from a synthetic resin or other suitable material capable of forming a thin walled tube that is sturdy, capable of folding or compression and that will assume its original tubular shape following deployment.

The proximal end and collar member 30 of the sleeve is connected with a proximal ring anchor 59, which may be in the form of an inflatable pyloric ring (FIG. 11). The proximal ring anchor 59 is sized for reception in the gastric antrum of the stomach 12 with the sleeve 16 extending into the small intestine 14. The inflatable pyloric ring anchor 59 is inflatably adjustable to prevent passage of the anchor through the pyloric sphincter and into the small intestine as well. The ring anchor 59 includes a central aperture 60, through which consumed food may pass into the sleeve 16, and a catheter aperture or passage 62. The configuration of the anchor allows for the complete system to be anchored in place allowing for the receipt of food from the stomach into the central aperture for passage into the sleeve. In another embodiment the collar member 30 can also include additional anchor mechanisms 58 for securing the sleeve within the stomach or duodenum. The anchor is envisioned to be any element that would allow for the anchoring for the complete system, including but not limited to an inflatable pyloric ring, non-inflatable pyloric ring, bolster member, tether, clip mechanism, tissue glue, staples, or any similar elements known in the industry.

In another embodiment the proximal end and collar member 30 is configured for removable attachment and reception in the gastric antrum of the stomach. The configuration can be any shape that will allow for the reception such as but not limited to a funnel, tubular, conical, cone shaped, cannula or similar shape. The configuration is such that it includes an anchor mechanism 58 for attachment to the stomach or the small intestines. The anchor mechanism 58 for attachment can be any method known in the art that includes but is not limited to bolster member, tether, clip mechanism, tissue glue, staples, sutures, or any combinations thereof.

As shown in FIGS. 1, 3, and 6 the catheter 28 is connected at its proximal end to the sideport 18 and passes through the catheter passage 62 configured in relation to the collar member 30 and into a catheter connection 64 in the outer membrane 44 of the malabsorption sleeve 16. In another embodiment the catheter connection can be incorporated into the collar member 30 of the sleeve for the transportation and delivery of nutrients to the patients small intestines. The catheter includes a lumen 66 that allows fluidic communication between the access portals 24 and the outer lumen 52 of the sleeve 16. The catheter connection 64 may be in the form of an aperture, through which the catheter 28 passes and extends into the outer lumen 52, or the catheter may terminate at or in spaced adjacent relation to the connection 64. In another embodiment the catheter is configured to be spaced adjacent to the malabsorption sleeve. The catheter is configured to allow for the transportation of nutrients, vitamins, water, or any other required elements to the patient. In another embodiment the catheter can also function as a tether for minimizing movement of the malabsorption sleeve, with connection between the malabsorption sleeve and the gastric port. The catheter is configured to allow for lengthening or shortening dependent on the desired length for use with the patient and to ensure secure anchoring.

As shown in FIG. 1, the intra-gastric or restriction balloon 20 is of conventional construction employed for reducing the volume or capacity of the stomach and imparting a feeling of fullness to the patient. The balloon can be configured to occupy between 5% and 95% of the volume of the stomach. The balloon 20 is connected with the side port 18 by a tether 68, having a length sized to anchor the balloon 20 in place within the patient's stomach. This serves to control the travel of the balloon and allows for quick and easy retrieval and/or adjustment of its size by injection or removal of a quantity of the fill solution. In another embodiment the tether can allow for the inflation of the balloon. The inflation of the balloon can be with any elements known in the industry including but not limited to gas, or liquid solution such as a saline solution. In addition to serving as an inflation tube the tube can also act a tether to minimize migration or movement of the balloon. The catheter 28 may serve as a tether to the collar member 30 or ring anchor 59, or a second tether may be provided between the side port 18 and the collar member 30. Alternatively, a single tether may be connected to both the gastric balloon 20 and the collar member 30 (or ring anchor 59 or sleeve 16).

A method of treating obesity in a patient involves providing a gastric restriction and malabsorption apparatus 10, positioning the apparatus so that it extends from the stomach 12 and into the small intestine 14 to prevent absorption of consumed food as it passes through, and delivering a nutritional supplement into a permeable portion of the device for absorption of nutritional and pharmaceutical compositions from the small intestine. The device includes an elongated bariatric sleeve 16 having proximal and distal ends and first and second elongated flexible tubular membranes. The first membrane has a proximal end, a distal end and an impermeable or water permeable sidewall defining a first lumen. The second membrane encircles the first tube and includes a proximal end, a distal end and a permeable sidewall defining a second lumen between the first and second tubes. The permeable sidewall includes an aperture or port for providing external access to the second lumen. An elongated, helical lumen support element is positioned within the first lumen in contacting relation with the first tube for maintaining the first lumen in an open position. A proximal anchor ring with a central aperture is connected to the proximal end of the sleeve. An anchor weight is connected to the distal end of the first flexible tube. A delivery catheter is connected between the gastric access port and the permeable outer membrane catheter connection.

The sleeve 16 and lumen support element 56 portions of the system 10 are first telescoped or compressed by pleating or coiling and threading the sleeve onto an insertion device such as an endoscope for insertion during an esophagogastroduodenoscopy (upper endoscopy or EGD procedure). In one embodiment, the system 10 is supplied as a sterilizable package in such an insertion configuration. In such a coiled, compressed configuration, the device may have a length of from about 20 cm to about 60 cm, and includes a central lumen capable of receiving a tip of an endoscope, laparoscope or other insertion tool. Alternatively, the coiled or compressed device may be inserted into the gastric lumen by means of an intragastric opening between the patient's outer skin surface and the stomach and threaded onto the endoscope within the gastric lumen via an introducer, laparoscope, flexible endoscope or other insertion tool.

Figure 8:
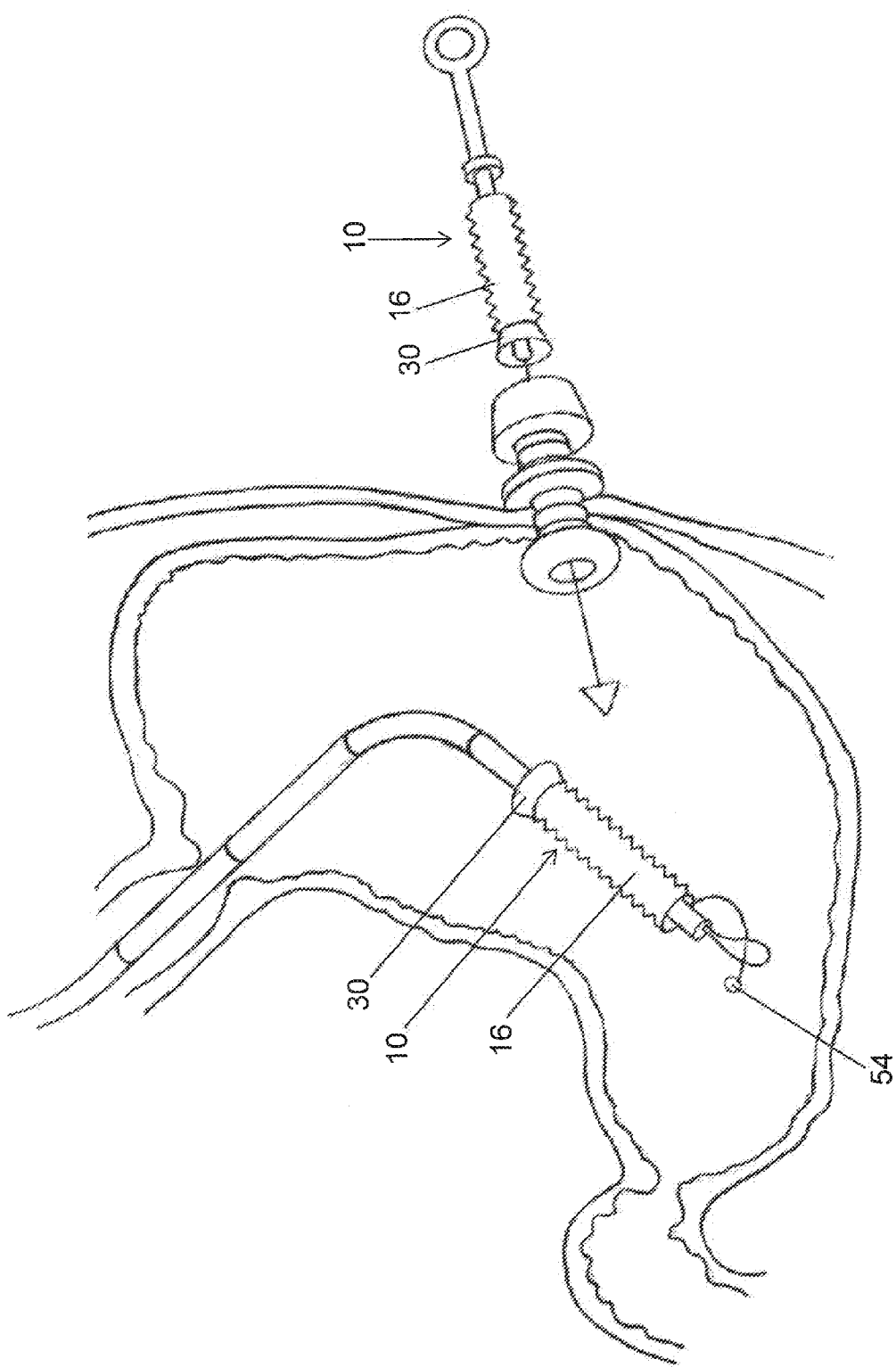
FIG. 8 is a view of the delivery mechanism for the malabsorption device.
Figure 9:
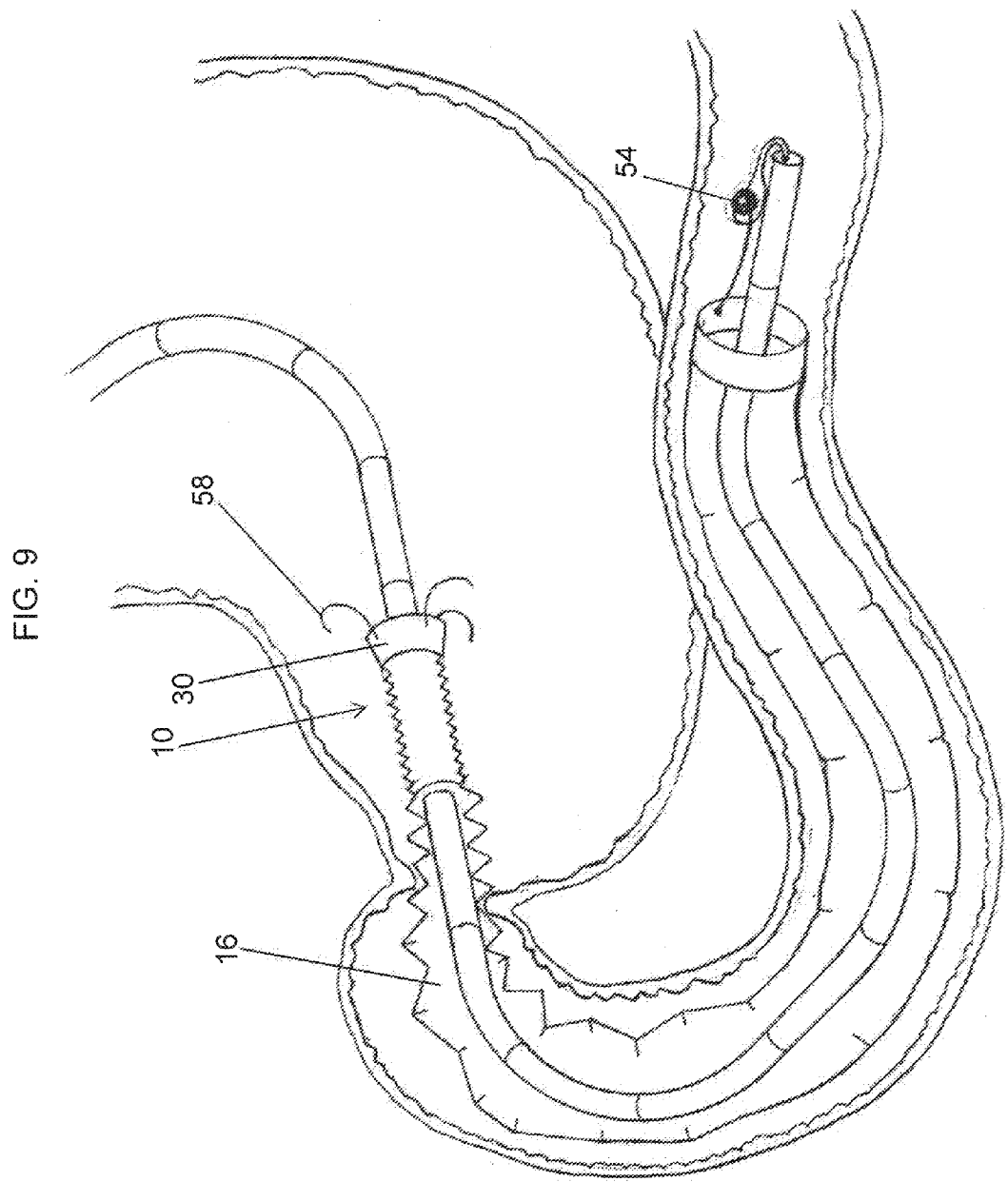
FIG. 9 is a view of the delivery mechanism for the malabsorption device.

The physician advances the endoscope through the central aperture 60 of the collar member 30 (or the ring anchor 59) and the first lumen 42 of the compressed device to the distal end of the device and deploys grasping forceps or other grasping device that may be introduced via the endoscope to grasp the distal anchor weight 54 at the distal end of the device. An overtube may be employed to push the entrained device off the end of the endoscope or introduction tool. In another aspect, the device may be equipped with a covered sheath that may be torn away by pulling a rip cord that pulls the sheath away allowing the device to deploy by assuming its remembered shape. As shown in FIG. 8 or 9, each anchor is equipped with a deployment string or wire and a control string or wire. The endoscope with the grasped device is advanced through the duodenum and into the middle portion of the jejunum where the proximal device is deployed by the deployment wire and the distal device is controlled by the control wire. When the distal end 38 of the inner membrane 34 has been positioned at a selected location corresponding to the length of the sleeve 16, the control wire is actuated to release the distal anchor weight. The weighted distal anchors may be temporarily secured into position by clips to prevent proximal migration of the device when it is deployed. The device opens and deploys, extending in both length, distally and proximally into the duodenal bulb, and in width. In one aspect, the device is sized to expand to a position in contact the inner wall of the small bowel, but does not exert excessive pressure on the wall of the small bowel.

The collar member 30 is positioned in adjacent superior relation to the pyloric valve and may be secured to the gastric antrum by stapling or suturing such as the anchoring mechanism 58. The proximal anchor ring 59 is fully deployed by inflating the ring when it is in the duodenum side of the pyloric valve. The endoscope is then backed out or withdrawn through the inner lumen 42 of the device and out through the central aperture 60 of the collar member 30 and ring anchor 59. After a period of time, the clips attached to the distal anchor fall off, because of their weight and peristaltic action of the small bowel. The clips may also be constructed of a dissolvable material.

The endoscope or insertion tool is used in similar fashion to introduce the intra-gastric balloon 20 through the side port 18 and to attach the balloon to the balloon tether 68. The balloon is deployed by introducing a syringe or cannula through the side port 18 and injecting a quantity of a saline solution, other liquid, gas or space occupying material into the balloon 20 until it reaches a desired size. The size of the balloon 20 may also be adjusted from time to time in the same manner by adding or removing selected volume quantities of the fill solution. The tether 68 attached to the side port 18 (gastric port) retains the balloon in position within the patient's stomach 12, so that it does not migrate to occlude the central aperture 60 of the collar member 30 or proximal ring anchor 59. The tether can further be lengthened or shortened dependent on the desired length to ensure a proper positioning of the balloon within the patient.

In use, nutritional supplements and pharmaceutical compositions are introduced as needed by injection or by tube into one or more of the fluid access ports 24. A quantity of a saline solution, water, or other inert solution may next be similarly introduced to carry the active compositions along the catheter 28 to and through the catheter connection 64 and into the outer lumen 52, where they exit into the duodenum for absorption by the small intestine.

While the preferred method involves introduction of the system 10 into the stomach 12 of a patient through the esophagus, it is foreseen that the systems may also be introduced through a gastrostomy or side port 18. Where the device is inserted via a gastrostomy or side port 18, the device may also be secured and attached at proximal end by sutures or staples introduced into the prepyloric antrum by a device introduced through the side port. After a period of time, the proximal end of the device may be internalized by staples or sutures to close the side port 18.

It is also foreseen that the order of operations could be varied as needed. For example, the gastric restriction balloon 20 could be deployed in the patient's stomach prior to installation of the malabsorption sleeve 16. In one aspect, the proximal anchor 58 may include sutures, staples or other mechanical means of attachment of the proximal end of the sleeve to the stomach. In another aspect, the distal anchor weight 54 may be replaced by anchoring staples, sutures or the like. In another aspect, radiopaque elements may be included to enable visualization of the device by X-ray or other imaging devices.

In one aspect, the device may also be employed in association with an adjustable collar member such as an inflatable or non-inflatable funnel. The funnel is installed in the duodenum or gastric antrum to receive food from the stomach. The food travels through the funnel and into the device, which prevents its absorption.

The device 10 is removable by reversing the previously described insertion method. Upon removal, food absorption is restored to its previous state. Advantageously, the device and installation procedure are minimally invasive and do not require significant surgical alteration of the anatomy. Following placement of the device patients may continue normal dietary intake and experience effective weight loss, without malnutrition.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

We claim:

1. A system for treatment of obesity in a patient having a gastric opening into the stomach from the external surface of the body, the system comprising:

a. an elongated sleeve having a proximal end and a distal end, b. the proximal end includes a collar member connected to the proximal end of the sleeve, the sleeve including a first elongated flexible tube having a proximal end, a distal end and a first sidewall defining a first lumen;

c. a second elongated flexible tube encircling a portion of the first elongated flexible tube and having a proximal end, a distal end and a permeable or a semi-permeable second sidewall, wherein an outer-facing surface of the first sidewall and an inner-facing surface of the second sidewall defines a second lumen;

d. an elongated helical member positioned within the first lumen in contacting relation with the first sidewall;

e. a proximal anchor ring having a central aperture, the proximal anchor ring connected to the proximal end of the sleeve with the central aperture disposed in coaxial relation to the proximal ends of the first and second flexible tubes, the proximal anchor maintains the sleeve in superior relation to a pyloric valve of the stomach;

f. an anchor weight connected to the distal end of the first flexible tube; and g. a delivery tube positioned at least partially in the second lumen and configured for delivery of a nutritional composition through the gastric opening and into the second lumen.

2. The system of claim 1, further including:
a. a liquid fillable balloon member configured for positioning within the stomach of the patient;
b. a tether member connected to the balloon member and configured to tether the balloon member to the gastric opening.

3. The system of claim 2, further including a tether member interconnecting the balloon member and the sleeve.

4. The system of claim 1, wherein the elongated sleeve further includes a memory member that allows for diameter expansion of the sleeve.

5. The system of claim 4, wherein the memory member is a coil attached to inner facing surface of the first sidewall.

6. The system of claim 1, further comprising: a tether connected to the proximal anchor ring and a gastrostomy port, wherein the gastrostomy port is configured to traverse the gastric opening.

7. The system of claim 1, further comprising:
a gastrostomy port;
a balloon member; and
a tether member connecting the gastrostomy port to the balloon member, wherein the balloon member is configured to be positioned within a stomach of a patient and the gastrostomy port configured to traverse the gastric opening.

8. The system of claim 1, wherein the proximal anchor ring is a tether for attachment to a gastric port.

9. The system of claim 1, wherein the collar member includes a catheter port.

10. The system of claim 1, wherein the collar member includes an anchoring member.

11. The system of claim 1, further comprising:
a gastrostomy port traversing the gastric opening, the gastrostomy port having an access portal, wherein the delivery tube extends through the access portal.

12. The system of claim 11, further comprising:
a second access portal in the external port configured for simultaneous access by a plurality of instruments or devices to a gastric environment of a patient.

13. The system of claim 1, wherein:
the first sidewall comprises an impermeable or semipermeable material to prevent absorption of consumed food; and
the second sidewall comprises a permeable material configured to allow passage of desired nutrients or pharmaceuticals from the second lumen through the second sidewall for absorption by a portion of a small intestine surrounding the second sidewall.

14. The system of claim 11, wherein the delivery tube tethers the proximal end collar to the gastrostomy port to minimize movement of the first elongated sleeve.

15. The system of claim 1, further comprising:
an intragastric displacement balloon; and
a tether connecting the intragastric displacement balloon to the elongated sleeve proximal end.

16. A method of treating a patient for obesity, comprising the steps of:
a. providing a bariatric malabsorption device having:
an elongated sleeve having a proximal end and a distal end, the sleeve including a first elongated flexible tube having a proximal end, a distal end and an impermeable sidewall defining a first lumen,
a second elongated flexible tube encircling the first elongated flexible tube and having a proximal end, a distal end and a permeable or a semi-permeable second sidewall, wherein an outer-facing surface of the impermeable sidewall and an inner-facing surface of the second sidewall defines a second lumen;
an elongated helical member positioned within the first lumen in contacting relation with the first sidewall;
a proximal anchor ring having a central aperture, the proximal anchor ring connected to a collar member at the proximal end of the sleeve and for anchoring the sleeve in superior relation to a pyloric valve of a stomach,
an anchor weight connected to the distal end of the first flexible tube; and
a delivery tube positioned at least partially in the second lumen and configured for delivery of a nutritional composition through the gastric opening and into the second lumen;

b. advancing an endoscope through the first lumen of the device to grasp the distal anchor weight;

c. advancing a portion of the endoscope with the grasped device through the gastric opening and into the duodenum and jejunum of the patient while positioning the proximal anchor ring in superior adjacent contact with the pyloric valve of the patient; and d. causing the endoscope to release the distal anchor weight and withdrawing the endoscope through the first lumen and the gastric opening.

17. The method of claim 16, further including the steps of:
a. providing a liquid fillable balloon member for use within the stomach of the patient;
b. advancing the grasped balloon member through the gastric opening and into the stomach of the patient; and
c. securing the balloon within the patient.

18. The method of claim 16, further comprising the step of forming the gastric opening by introducing a gastrostomy port.

* * * * *